United States Patent [19]

Macourt

[11] 4,225,314
[45] * Sep. 30, 1980

[54] CHEMICAL ANALYSIS AND MINERAL PROSPECTING

[76] Inventor: Denis J. C. Macourt, 73, Dickson Ave., Artarmon 2064, New South Wales, Australia

[*] Notice: The portion of the term of this patent subsequent to Jan. 30, 1996, has been disclaimed.

[21] Appl. No.: 884,956

[22] Filed: Mar. 9, 1978

[30] Foreign Application Priority Data

Mar. 9, 1977 [AU] Australia .................. PC9339

[51] Int. Cl.² .......... G01N 1/10; G01J 3/00; G01V 5/00; G01N 33/24
[52] U.S. Cl. .............. 23/230 EP; 250/255; 356/36; 356/316
[58] Field of Search ........ 23/230 EP, 232 R, 253 PC; 250/255, 253; 356/85, 86, 36, 316

[56] References Cited

U.S. PATENT DOCUMENTS

| | | | |
|---|---|---|---|
| 2,330,021 | 9/1943 | Arthur | 23/230 EP X |
| 2,330,829 | 10/1943 | Lundberg et al. | 23/230 EP X |
| 2,591,737 | 4/1952 | Souther, Jr. | 23/230 EP X |
| 2,918,579 | 12/1959 | Slobod et al. | 23/230 EP X |
| 3,118,299 | 1/1964 | Worthington | 23/230 EP X |
| 3,455,144 | 7/1969 | Bradley | 23/230 EP X |
| 3,759,617 | 9/1973 | Barringer | 23/230 EP X |
| 3,868,222 | 2/1975 | Barringer | 23/230 EP |
| 4,056,969 | 11/1977 | Barringer | 23/230 EP X |
| 4,066,891 | 1/1978 | Gray | 250/255 X |
| 4,136,951 | 1/1979 | Macourt | 356/36 |

Primary Examiner—Joseph Scovronek
Attorney, Agent, or Firm—Curtis Ailes

[57] ABSTRACT

A sample stream of liquid representative of the environment such as sea water or lake water or drilling mud is subjected to the passage therethrough of an inert carrier gas to entrain chemical components and particulate matter which is then removed from the sample stream for analysis of the chemical components and particulate matter.

8 Claims, 1 Drawing Figure

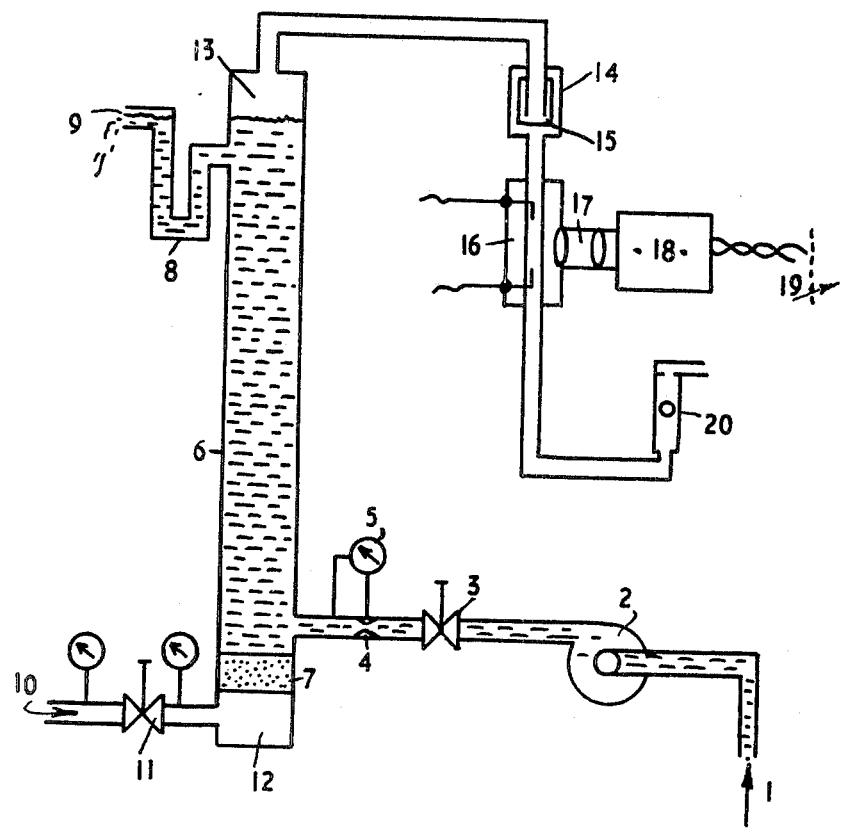

CHEMICAL ANALYSIS AND MINERAL PROSPECTING

The present invention pertains to the extraction of chemical components from their environmental situation—and provides a method of detecting the presence of, and determining (e.g. spectroscopically) the nature of, such chemical components. The invention has particular relevance to the prospecting for, and location of, deposits or accumulations (hereafter simply called deposits) of uranium and related minerals, as well as hydrocarbon (e.g. oil, natural gas) deposits which have, as a common feature, the presence of (i) radon (atomic No. 88 and atomic weight 222), and (ii) other elements and minerals (as exemplified by halogens, in particular iodine). The subject matter of the present patent application is closely related to the subject matter of prior U.S. Pat. applications Ser. Nos. 739,110 filed Nov. 5,1976, now U.S. Pat. No. 4,136,951 dated Jan. 30, 1979, and 817,498 filed July 20, 1977 by the same inventor.

The anomalous occurrence of radon gas—and other elements and minerals such as halogens, in particular iodine—around deposits of uranium (and associated minerals) and hydrocarbons is well known, and has been used by numerous prior investigators in the search for such deposits. However the practice of such investigators has been mainly directed to the study of on-shore deposits—and has involved techniques which, in the main, are laborious, time-consuming, labour-intensive and expensive. In addition, none of such prior techniques are applicable to the search for deposits of uranium and associated minerals, and hydrocarbons, under large bodies of water. It is towards this latter purpose that the present invention is principally directed.

For convenience, the area of investigation to which the present invention particularly relates will be qualified by the expression "off-shore". It will be understood that, whilst this expression principally connotes an investigation carried out in respect of sea and/or ocean waters, it is not to be construed as confined thereto (obviously inland bodies of water are not excluded—nor, in point of fact, is any material having the characteristics of a liquid, such as a stream of drilling mud, to which the method of the invention can be applied). It is among the objects of the invention to provide a process whereby off-shore investigation for uranium and associated minerals, and hydrocarbon deposits (e.g. oil, natural gas) is carried out speedily, efficiently and economically. Also, as foreshadowed heretofore, the invention provides for the extraction of chemical components (as radon gas, halogens such as iodine) from their environmental (off-shore) situation, and for the spectroscopic or other detection of such components.

In its broadest aspect, the invention provides a method of extracting a chemical component from an off-shore environmental situation comprising the steps of subjecting a stream of sea water, or other liquid from such a situation, to passage therethrough of a chemically inert carrier gas whereby the chemical component contained in said stream, and any particulate matter associated therewith, is entrained by the said gas; removing the gas, entrained component, and particulate material if any from the sea water or other liquid; and, as required, separating the particulate material if any from the gas and chemical component. In a further aspect, the invention provides a method of detecting the presence of a chemical component in an off-shore environmental situation comprising the steps of subjecting a stream of sea water, or other liquid from such a situation, to passage therethrough of a chemically inert carrier gas whereby the chemical component contained in said stream, and any particulate matter associated therewith, is entrained by the said gas; removing the gas, entrained component, and particulate material if any from the sea water or other liquid; separating the particulate material if any from the gas and chemical component; passing the gas and chemical component into a plasma, and spectroscopically examining the light emitted therefrom. Other aspects of the invention will emerge from the ensuing description.

The chemical component to be extracted and detected in accordance with the invention occurs, in its off-shore environment, in a variety of forms. Thus, as appropriate, it may itself be gaseous, solid, in solution, or in suspension—or alternatively, it may be coated (i.e. absorbed) on the surface of suspended particulate material. In the ensuing description, reference is particulary made to a (radon) component which is both in solution and so coated or adsorbed.

As used in this specification, the term "coating" or "radon coating", or "halogen coating", will be used to cover a wide variety of possible combinations including individual, or numbers, of radon or halogen atoms or molecules (or condensation neuclei) adhering to, or being adsorbed on, the surface(s) of a particle—and, in addition, actual coatings of radon or halogen atoms or molecules (or condensation neuclei) in which the particle itself is partially or substantially completely covered or enveloped with a thin layer of radon or halogen atoms or molecules (or condensation neuclei).

The invention will now be described with sequential reference to preferred sub-generic details, a specific operation as illustrated by reference to accompanying drawing, and a modification. As a general prelude thereto, it is emphasised that such ensuing description is not to be limitatively construed.

1. RADON DETECTION

Dealing firstly (and sub-generically) with the instant method as applied to the detection and extraction of radon, it is initially pointed out that such method enables the continuous detection of radon to be achieved from a boat operating on the water. This therefore makes the method of the invention highly suitable for both regional and detailed prospecting over large areas for anomalous concentrations of radon emanating from accumulations of uranium and hydrocarbons under water. The detection of such anomalous emanations and, with a suitable means of navigation, the accurate determination of their locations within a region represents a major step in the search for these deposits (and will accurately indicate an area in which further detailed geophysical work, such as seismic surveying or drilling, should be carried out). In addition, under suitable conditions, the determination of such anomalies may lead to the direct discovery of commerically viable deposits of such minerals or hydrocarbon accumulations.

In connection with this form of the invention, it is known that atoms or molecules of radon gas, being normally in the form of ions, are soluble in water and may also, by reason of their charge, adsorb on the surface of any particulate and/or colloidal matter held in suspension in the stream of water (these are the two principal modes of occurrence foreshadowed heretofore). This aspect of the invention features
(i) entrainment of the radon gas, or the radon-coated suspended particulate material, by passage, through the stream of sea water, of finely dispersed bubbles of inert carrier gas;
(ii) removal of the inert gas, radon component, and particulate matter if any, from the stream;
(iii) heating of the particulate material (if any) to release the radon coated thereon;
(iv) passage of the radon and the inert gas into a plasma;
(v) spectroscopic analysis of the light emitted from the plasma.

Proceeding, a stream of sea water, which may be in passage or stationary, is itself subjected to passage, therethrough, of finely dispersed bubbles of helium or argon (the inert gas however need not be a noble gas). By this passage, encumbent particulate and/or colloidal matter (for convenience, the former term is solely employed hereafter) is scavenged from the stream, the particulate matter initially becoming entrainingly attached to the bubbles in a manner similar to that employed in mineral flotation. In the case of dissolved radon gas, entrainment is effected by such gas itself coming out of solution into the helium or argon bubble by diffusion through the wall of the said bubble.

As the inert gas bubble bursts through the surface of the water, the ejected particulate material is carried away by a gaseous stream established above the surface of the water. The said gaseous stream—containing both adsorbed particulate and gaseous radon molecules which, by reason of their intrinsic ionic nature, will tend to cluster and agglomerate with other uncharged molecules and condensation nuclei—is in a particularly suitable form for analysis.

On this point, it should be noted that, unless the analysis is carried out very shortly after the particles are collected, the natural decay of the collected radon will cause the apparent magnitude of the anomaly to be severely reduced once the radon is removed from the area in which it is being given off. Most importantly, undue delay in analysis may preclude radon being detected at all.

Furthermore, unless the analytical technique used is specific for radon, confusion could result in the interpretation of the results. For example, the Bismuth isotope, having an atomic weight of 214, is a decay product of radon gas which has a half-life of several years. This decay product appears ubiquitously throughout the atmosphere and in the sea. Therefore if an inadequate technique is used, this can give misleading anomalous radioactivity which may not be due to radon at all.

The radon coating is released from the particles by neutralizing the electrical charge attaching the atoms or molecules (or condensation neuclei) to the particles and thereby volatilising the coating. This is carried out by heating the particles in a suitable oven i.e. the particles are subjected to pyrolisation, the dust particles in the oven being trapped on a porous sintered filter in which the pore size is finer than the size of the collected particles. In this way the particles are retained by the filter and only the gaseous products of pyrolisation are carried forward in the inert gas stream beyond the filter. The temperature of the oven is as low as possible (a temperature of the order of 150° C.—or less—is invariably adequate) to release the atom(s) or molecule(s) of radon in the coating, by the process of thermophoresis.

In this connection, such temperature should also be low enough to avoid chemical interaction between the molecules being released yet high enough to cause rapid release and avoid "smearing" of the released material.

Alternatively, the radon coating et al may also be volatilised by the employment of a primary plasma in which the particulate material is retained, and the adsorbed material being volatilised is separated therefrom and passed on to a next stage—where analysis of the volatilised material is carried out.

From the foregoing, it will be observed that a plasma need not be employed to obtain the release or volatilisation of the radon coating (although if it is desired to also analyse the particulate coatings for other adsorbed molecules of low volatility, it may be advantageous to do so). Volatilisation of the adsorbed material may also be accomplished by using a laser if desired.

In the next stage, the released gases and volatilised materials are then transported immediately to a plasma (or secondary plasma) which is viewed by a conventional spectrometer or other suitable instrument which permits the emission or absorption of radon to be observed and measured. The plasma may be either a direct current discharge or an alternating current discharge—and in the latter case, low frequencies, radio frequencies, and microwave frequencies may be used as desired.

When the analysis of the light emitted from the above-mentioned plasma is carried out, in accordance with this embodiment, using the methods of atomic emission spectroscopy, the strongest emission line for radon is at 434.96 nanometers (nm) whilst the next strongest line is at 745.00 nm.

The first of these emission lines is adjacent to the emissions of a well-developed C-H band structure, which emission ends at approximately 433.5 nm at the longer end, and could cause interference. This is particularly relevant if the instant method is used for prospecting for oil or natural gas where hydrocarbons could be adsorbed on the surface of particles—and which, in turn, would give significant emission in the well known C-H and C-N bands, the latter of which occurs at approximately 388 nm.

The resolution of the strongest emission line at 434.96 nm will depend on the quality of the particular spectrometer used, but there are several techniques well known to those skilled in the art, for achieving the desired resolution and separation from the above-mentioned C-H band. Additionally the emission line at 745.00 nm or another radon emission line nearby at 705.54 nm, are both relatively free from interference from other continuums and these lines can be used either separately or as a measure of differentiating the radon emission at 434.96 nm from the above-mentioned C-H band emission.

A suitable apparatus for performance of the just-described method is illustrated hereafter.

2. HALOGEN DETECTION

This form of the invention is described with particular reference to the detection of iodine (especially) and bromine—which, just as in the case of radon, has been found to be associated, in anomalous concentrations, with deposits of uranium, oil, natural gas etc. In cases where these deposits are located off-shore, extraction and detection of such iodine concentrations, in accordance with the instant method, can lead to location and subsequent development of such deposits.

Detail-wise, the iodine component in a stream of sea water can be entrained by finely dispersed bubbles of helium or argon (or other inert gas) passed through the said stream in a manner similar to that described heretofore i.e. the particulate material, with iodine adsorbed thereon, will become attached to the bubbles, and/or the iodine molecule, by virtue of its normal sublimation and vapour pressure, will diffuse through the wall of the bubble. Following entrainment in the inert carrier gas, heating if required (to separate the iodine from its associated particulate material if any) and spectroscopic analysis (whereby errors—that could flow from the natural sublimation of the iodine adsorbed on the entrained particles—are forestalled) are also carried out in the manner above described.

In this form of the invention—when the analysis of the light emitted from the plasma is carried out by atomic emission spectroscopy—the most suitable emission line for iodine is at 608.2 nanometers (nm) whilst other suitable lines are at 546.5 nm and 533.8 nm. For bromine, the most suitable emission line is at 478.5 nanometers.

In the detection of iodine by emission spectroscopy, the wave lengths of light produced by electrode decay should not interfere with the iodine spectral lines. It has been found that this is best achieved by the use of electrodes of solid platinum or platinum/indium. Again, a suitable apparatus is hereafter described.

3. AN ILLUSTRATED EMBODIMENT

Hereunder, the detection of radon and/or halogen (iodine) is described with reference to the annexed illustrative drawing. In again emphasising that such description is by way of example only, it is also recorded that a schematic type of illustration is employed because the individual integers of the illustrated apparatus are themselves conventional in structure.

The drawing schematically depicts an apparatus whereby the instant method may be carried out.

In carrying out the invention with the aid of apparatus as so illustrated, the sea water, from a selected offshore environmental situation, enters at inlet (1) and is pumped by pump (2) out through throttling valve (3) and venturi flow meter (4) into column (6), rising through "U" tube lock (8) to discharge point (9). The flow is to be constant as measured by flow meter (5). At the base of column (6) there is a sintered porous block (7). Inert carrier gas (e.g. helium) enters through inlet (10) under pressure and is passed through reducing valve (11), to enter chamber (12) underneath porous block (7) at a pressure sufficient to cause the gas to diffuse through the block (7) and to prevent the ingress of water into chamber (12). Because of the fineness of the sintering in block (7) (e.g. of the order of <0.5 micron), the gas is introduced into the column of water (6) as extremely small bubbles and rises through the column, with the flow of water to be discharged, into collecting volume (13) which latter is effectively at atmospheric pressure. A connecting pipe leading from volume (13) is arranged so as to prevent the direct carry over of water droplets into sintered porous filter (15) which is contained in a thermostatically controlled oven (14) (at a temperature of, for example 100°-200° C.). The size of the smallest particle reaching the sintered filter should be greater than the pass size of the filter. In itself, the filter is removable from the oven for cleaning and emptying—and can be sealingly reassembled with equal facility.

Radon present in column (6)—either in dissolved or adsorbed condition as indicated hereinbefore—is entrained by the bubbles of inert gas and, after being released into volume (13), is conveyed through the said connecting pipe to the oven. In the case of the dissolved radon (present in the inert gas bubbles as molecules recovered from solution by diffusion as above described), pyrolisation in the oven (14) will not be required, and the gas and radon may be simply passed forward for analysis. In the case of the adsorbed radon, pyrolisation and separation are effected per medium of oven (14) and filter (15), the thus released radon gas being thereafter ready for said analysis.

The radon gas, for analysis, passes to a plasma (16) (containing electrodes as illustrated or a quarter wave resonance cavity) where the resulting plasma is viewed, through a conventional optical arrangement (17), by a conventional spectrometer or monochrometer (18), the resulting signal being fed to an amplifier and recorder (19). Flow gauge (20), in the efflux circuit of plasma cell (16), ensures a constant rate of flow—and hence calibration.

If required, the apparatus as illustrated may be coupled to a suitable navigating system. In this way the output of the spectrometer (or monochrometer) can be co-related with the position of a vessel from which the investigation is being carried out.

In the description of the illustrated embodiment, the chemically inert carrier gas is specified as helium. However, in lieu thereof, there may be employed any other such gas(es), noble or otherwise, as exemplified by argon, and gaseous, mixtures (the latter possibility in turn being exemplified by an argon/helium mixture). The electrodes (of the electrode plasma) are constructed from materials that are free of those elements that are being viewed by the spectrometer; specifically, in the embodiment illustrated, the electrodes are of platinum.

In referring to the spectrometer, the opportunity is taken to underscore the fact that the invention is not limited in respect of the type of spectrometer (or method of spectroscopic analysis) employed. In this latter connection, it is also mentioned that, whilst spectroscopic analysis is certainly preferred, the invention, as made clear in the opening description, does not overlook analysis by other techniques-such as gas chromatography (in which operation, suitable "gating" of the gases, by valves, would be required to facilitate proceedings).

4. MODIFICATION

As foreshadowed in the definition (heretofore) of the term "off-shore", the invention may also be applied to (the analysis of) liquids such as drilling mud. Specifically, in this connection, it finds application in the logging of drill holes used for the tapping of underground reservoirs of hydrocarbons.

Conventionally a heavy mud is used to contain the drill bit and stem in the hole, and to carry away the cuttings of the drilling operation. This mud will contain increasingly anomalous concentrations of radon, iodine and other chemicals as it approaches the area where a reservoir of hydrocarbons exists. It is commonly accepted practice to examine the drill mud and chippings for traces of hydrocarbon gases and liquids by gas chromatography and fluorescence techniques and these procedures are well known. The detection limits are, however, of the order of 1 ppm and the procedures are laborious and not continuous in operation.

I have found that, by bubbling inert gas (such as helium) through a sample stream of drilling mud—preferably with dilution of the said stream to facilitate bubbling passage of the inert gas therethrough, and recovery of such gas before the mud flows out through the overflow pipe (of apparatus such as hereinabove illustrated)—degassing of the radon and/or halogen (or other component) out of the system, followed by spectroscopic or other analysis thereof, can be achieved in the manner above described. At all levels, the results (in respect of criteria such as the information made available, and the speed and sensitivity of operation) are entirely satisfactory. Specifically, detection limits of the order of 1 ppb can be achieved.

In this way a continuous monitoring of the progress of drilling can be carried out which ignores hydrocarbon traces in rocks containing large amounts of organic material and gives an important indication of the hole approaching reservoir structures where anomalous accumulations of uranium and other soluble elements and chemicals have arisen in the same way as oil and natural gas. As the mud cycle time from bit to surface may be of the order of 1–2 hours the analysis will be sufficiently fast to give warning of approaching zones of interest and sufficiently selective when looking at multiple channels of radon, iodine and hydrocarbons to considerably reduce the possibility of of erroneous conclusions.

It will of course be appreciated that the foregoing separately presented description of radon detection and halogen detection, in the paragraphs respectively numbered 1 and 2, has been principally adopted for convenience; in the practice of the invention (as suggested in paragraph 3) the inert gas bubbled through a sample of liquid can entrain both components. It should also be understood that, whilst the foregoing description generally emphasises the extraction and detection of radon and halogen (principally iodine) components, the invention should not be regarded as confined thereto; in this connection, the "other elements and minerals" (see above) envisage metallic components such as strontium. Still further, it is re-emphasised that the term "stream", in the expression "stream of sea water . . . ", connotes bodies or samples both moving and stationary. Finally, apropos the illustrated apparatus, it is mentioned that variations thereof (apart from those already indicated) are contemplated; for example it is envisaged that preparation of the chemical component for spectroscopic or other analysis can be effected without an oven.

In broad summary, the invention, in its primary method aspects, is as hereinbefore broadly defined—with the gaseous, or particulate matter-coated, chemical components (to be extracted et al from the sea water or other liquid environment) sequentially subjected to (i) entrainment by an inert carrier gas, (ii) removal from the liquid environment, (iii) heating (if necessary), and (iv) analysis (if required for purposes of detection). However, the invention should also be understood as embracing:

(a) a method for continuously detecting the presence of a radon and/or halogen component in an off-shore environmental situation comprising the steps of subjecting a stream of sea water, or other liquid from such a situation, to passage therethrough of dispersed bubbles of a chemically inert carrier gas whereby the radon and/or halogen component contained in the stream, whether coated to particulate material and/or otherwise, is entrained by the said gas; removing the gas, component and particulate material if any from the stream; heating the particulate material if any to release the radon and/or halogen component coated thereon, and separating the said particulate material from the released component and the carrier gas; passing the carrier gas and component into a plasma and spectroscopically examining the light emitted therefrom;

(b) an apparatus for extracting a chemical component from an off-shore environmental situation comprising, in combination, means for collecting a stream of sea water or other liquid from such a situation; means whereby a chemically inert carrier gas is bubbled through such stream thereby entraining the chemical component and particulate material if any associated therewith; and means whereby the gas, chemical component and particulate material if any, upon removal from the stream, are conveyed therefrom for separation of particulate material (as and if required);

(c) an apparatus for detecting the presence of a chemical component in an off-shore environmental situation, comprising, in combination, means for collecting a stream of sea water or other liquid from such a situation; means whereby a chemically inert carrier gas is bubbled through such stream thereby entraining the chemical component and particulate material if any associated therewith; means whereby the gas, chemical component and particulate material if any, upon removal from the stream, are conveyed therefrom for separation of particulate material (as and if required); and a plasma to which the gas and chemical component are conveyed for spectroscopic examination.

I claim:

1. A method for prospecting for uranium or hydrocarbons by continuously detecting the presence of at least one normally gaseous radon or halogen component in an off-shore liquid as an indicator of the presence of uranium or hydrocarbons comprising the steps of subjecting said liquid to passage therethrough of dispersed bubbles of a chemically inert carrier gas of a type useful in plasma emission spectroscopy whereby said gaseous component contained in said liquid and any particulate matter components containing said gaseous component adsorbed as a coating thereon are entrained by said inert gas; removing said inert gas and said entrained components from said liquid; treating said particulate material to release said gaseous component coated thereon, and separating said particulate material from said gaseous component and said carrier gas; passing said carrier gas and said gaseous component into a plasma and spectroscopically examining the light emitted therefrom for the presence of spectral lines characteristic of at least one of said normally gaseous chemical components.

2. A method as claimed in claim 1 wherein
the chemically inert carrier gas consists of at least one member of a group consisting of helium and argon.

3. A method as claimed in claim 1 wherein the off-shore liquid is sea water.

4. A method as claimed in claim 1 wherein the off-shore liquid comprises drilling mud from an off-shore exploratory drilling operation.

5. A method as claimed in claim 4 wherein the off-shore liquid consists essentially of drilling mud diluted with sea water.

6. A method as claimed in claim 1 wherein said normally gaseous component is radon.

7. A method as claimed in claim 1 wherein said normally gaseous component is iodine.

8. The method of claim 1 wherein the step of treating said particulate material to release said gaseous component coated thereon is carried out by heating said particulate material.

* * * * *